US011369389B2

(12) United States Patent
Palmatier et al.

(10) Patent No.: US 11,369,389 B2
(45) Date of Patent: Jun. 28, 2022

(54) SURGICAL INSTRUMENT AND METHOD

(71) Applicant: WARSAW ORTHOPEDIC INC., Warsaw, IN (US)

(72) Inventors: Stanley T. Palmatier, Olive Branch, MS (US); William D. Armstrong, Memphis, TN (US); Nicholas M. Benson, Cordova, TN (US); Grady S. Davis, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 129 days.

(21) Appl. No.: 16/725,250

(22) Filed: Dec. 23, 2019

(65) Prior Publication Data

US 2020/0129190 A1    Apr. 30, 2020

Related U.S. Application Data

(63) Continuation of application No. 14/853,658, filed on Sep. 14, 2015, now Pat. No. 10,548,618.

(51) Int. Cl.
*A61B 17/16* (2006.01)
*A61B 17/00* (2006.01)

(52) U.S. Cl.
CPC ............... *A61B 17/1671* (2013.01); *A61B 2017/00991* (2013.01)

(58) Field of Classification Search
CPC ............... A61B 17/285; A61B 17/295; A61B 17/32002; A61B 17/320028; A61B 17/320092; A61B 17/16; A61B 17/1606; A61B 17/1604; A61B 2017/32004; A61B 17/2812

See application file for complete search history.

(56) References Cited

U.S. PATENT DOCUMENTS

| 4,962,770 A | * | 10/1990 | Agee | A61B 17/320036 128/898 |
| 5,290,309 A | * | 3/1994 | Kothe | A61B 17/2833 606/207 |
| 5,306,284 A | * | 4/1994 | Agee | A61B 17/320036 606/170 |

* cited by examiner

*Primary Examiner* — Anu Ramana
(74) *Attorney, Agent, or Firm* — Sorell, Lenna & Schmidt, LLP

(57) ABSTRACT

A surgical instrument includes a first member defining an axis. A second member is axially translatable relative to the first member. A cutting element is connected with the second member and has a cutting surface. The cutting element is rotatable relative to the second member to transversely move cut tissue. Systems, implants and methods are disclosed.

20 Claims, 14 Drawing Sheets

SURGICAL INSTRUMENT AND METHOD

CROSS REFERENCE TO RELATED APPLICATIONS

This application is a continuation of U.S. patent application Ser. No. 14/853,658, filed on Sep. 14, 2015, which is hereby expressly incorporated herein by reference, in its entirety.

TECHNICAL FIELD

The present disclosure generally relates to medical devices for the treatment of musculoskeletal disorders, and more particularly to a surgical system for preparation of a surgical site and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, laminectomy, corpectomy and discectomy, decompression of nerve tissue can be provided and/or fusion and fixation treatments may be performed that employ implants to restore the mechanical support function of vertebrae. Surgical instruments are employed, for example, to prepare and/or remove tissue surfaces in connection with surgical treatment. Surgical instruments are also employed to engage implants for disposal with the tissue surfaces at a surgical site. This disclosure describes an improvement over these prior technologies.

SUMMARY

In one embodiment, a surgical instrument is provided. The surgical instrument includes a first member defining an axis. A second member is axially translatable relative to the first member. A cutting element is connected with the second member and has a cutting surface. The cutting element is rotatable relative to the second member to transversely move cut tissue. Systems, implants and methods of use are disclosed.

BRIEF DESCRIPTION OF THE DRAWINGS

The present disclosure will become more readily apparent from the specific description accompanied by the following drawings, in which.

DETAILED DESCRIPTION

Figure 1:
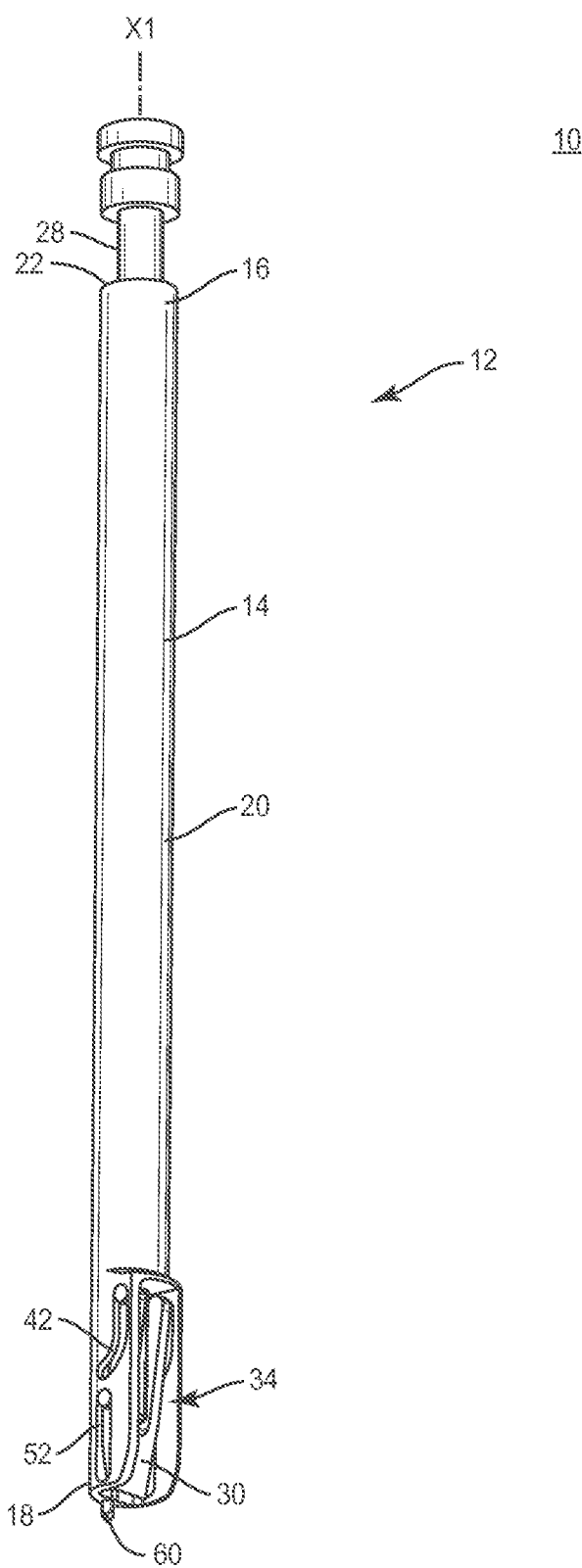
FIG. 1 is a perspective view of components of one embodiment of a surgical system in accordance with the principles of the present disclosure.
Figure 2:
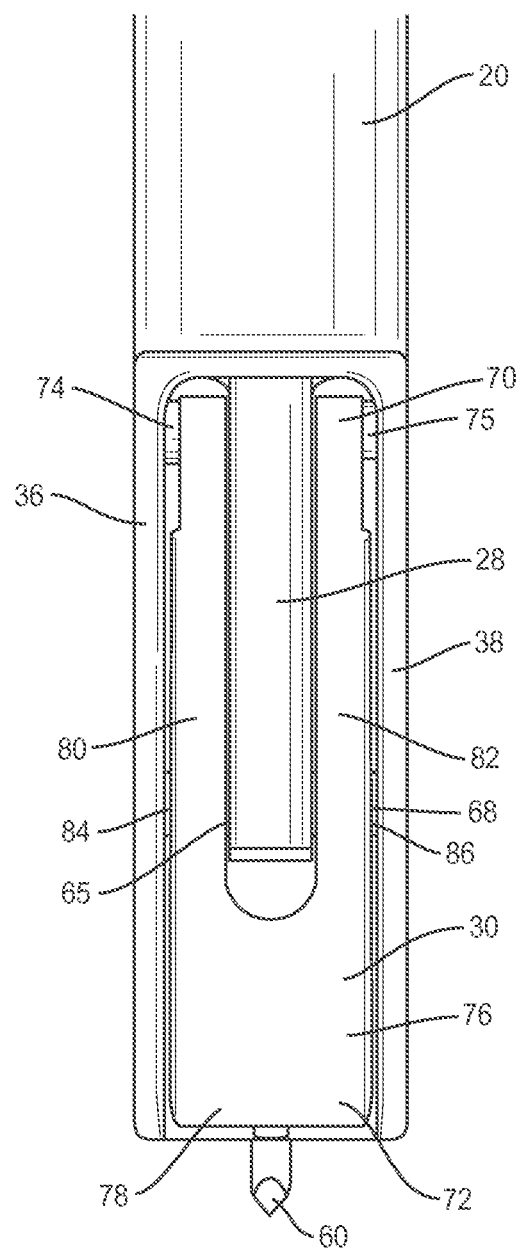
FIG. 2 is a break away view of the components shown in FIG. 1.
Figure 3:
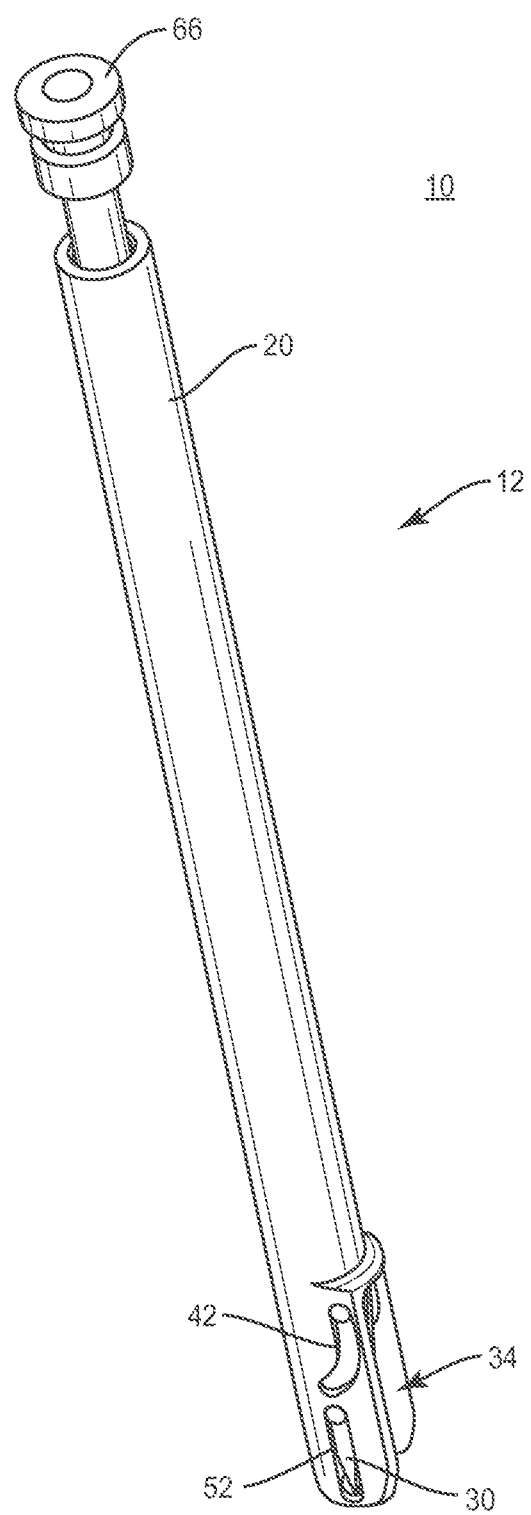
FIG. 3 is a perspective view of the components shown in FIG. 1.
Figure 4:
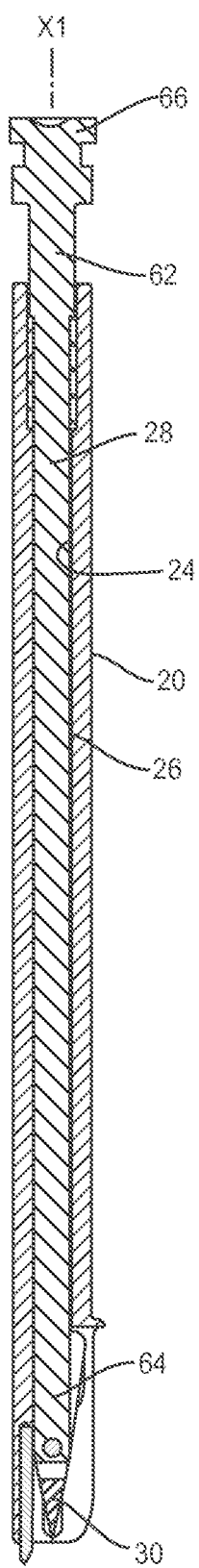
FIG. 4 is a cross section view of the components shown in FIG. 1.
Figure 5:
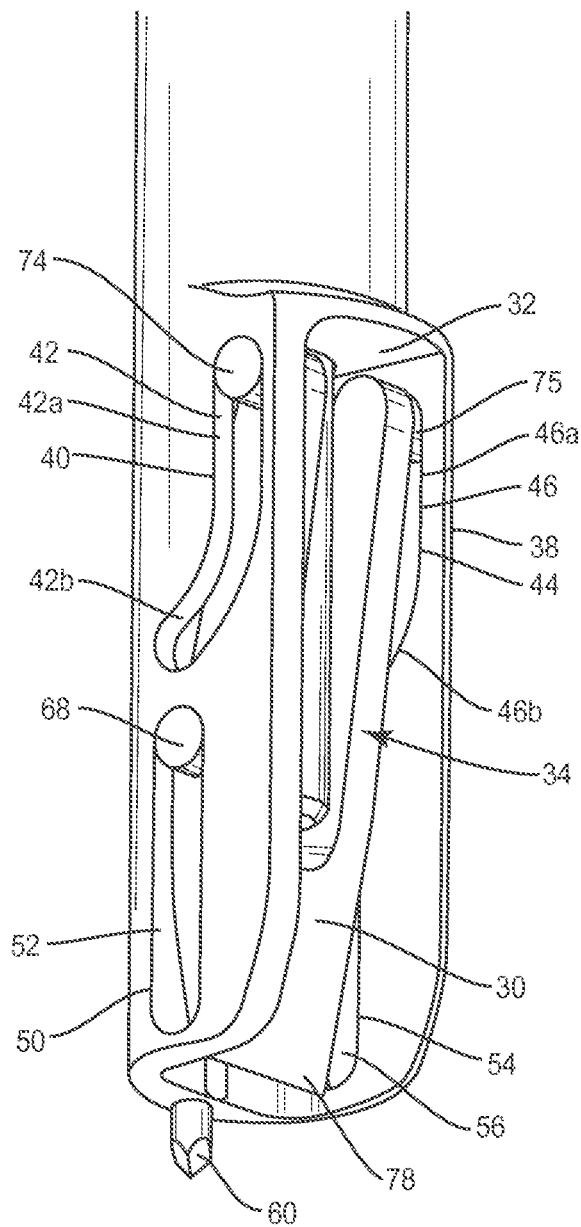
FIG. 5 is an enlarged, break away view of the components shown in FIG. 1.

The exemplary embodiments of the surgical system and related methods of use disclosed are discussed in terms of medical devices for the treatment of musculoskeletal disorders and more particularly, in terms of a surgical system for preparation of a surgical site and a method for treating a spine.

In some embodiments, the surgical system includes a surgical instrument, such as, for example, an articulating and/or rotating cutting instrument. In some embodiments, the surgical system includes a surgical instrument, such as, for example, a spring-loaded, articulating and/or rotating osteotome. In some embodiments, the surgical instrument includes a spring-loaded, articulating/rotating osteotome that includes a slap-hammer interface at a proximal end, which provides greater control and accuracy for removal of the facets.

In some embodiments, the surgical system includes a cutting instrument having a positive stop to prevent over-extension into nerve roots and vascular anatomy. In some embodiments, the surgical system includes a cutting instrument having a built-in awl to anchor the cutting instrument. In some embodiments, the surgical system includes a cutting instrument having a self-retracting blade. In some embodiments, the surgical system includes a cutting instrument having an articulating and/or rotating blade that separates a facet from vertebral tissue by engaging and driving the facet from the vertebral tissue after cutting it away. In some embodiments, the surgical system includes a cutting instrument having a slap hammer interface. One or more of the above configurations provide practitioner control during cutting of the facet in and around sensitive anatomy of a patient.

In some embodiments, the surgical instrument includes suction to facilitate material removal. In some embodiments, the surgical instrument includes a navigation device to facilitate positioning and/or tracking of components of the surgical system. In some embodiments, components of the surgical instrument include a fiber-optic light and a camera mounted with an outer housing. In some embodiments, the camera includes a miniature camera. In some embodiments, the cutting surfaces or blades of the components of the surgical instrument, as described herein, can include, such as, for example, diamonds, spikes and/or sandpaper.

In some embodiments, one or all of the components of the surgical system are disposable, peel-pack, pre-packed sterile devices that can be used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system 10 including a surgical instrument 12.

The components of surgical system 10 can be fabricated from biologically acceptable materials suitable for medical applications, including metals, synthetic polymers, ceramics and/or their composites. For example, the components of surgical system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), calcium sulfate, or other resorbable polymers such as polyaetide, polyglycolide, polytyrosine carbonate, polycaroplaetohe and their combinations.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

The components of surgical system 10 including surgical instrument 12 can be employed, for example, with mini-open and open surgical techniques to prepare a surgical site including tissue in connection with a surgical procedure for delivery and introduction of instrumentation and/or an implant at a surgical site within a body of a patient, for example, a section of a spine. In some embodiments, the components of surgical system 10 may be employed with surgical procedures to treat patients suffering from a spinal disorder to provide decompression of the spinal cord, nerve roots and/or adjacent vascular anatomy. In some embodiments, the components of surgical system 10 may be employed with surgical procedures, such as, for example, laminectomy, laminoplasty and/or stabilization of vertebral tissue, such as, for example, lamina, transverse process, pars interarticularis, facet or spinous process portions of one or more vertebral levels.

Surgical instrument 12 includes a member, such as, for example, a body 14 that extends between an end 16 and an end 18. Body defines an axis X1 and includes a housing 20. In some embodiments, housing 20 may have cross section configurations, such as, for example, oval, cylindrical, triangular, square, polygonal, irregular, uniform, non-uniform, offset, staggered, undulating, arcuate, variable and/or tapered. Housing 20 includes a wall 22. Wall 22 includes a thickness and an inner surface 24. Surface 24 defines a cavity, such as, for example, a channel 26 extending along axis X1. Channel 26 extends between end 16 and end 18. Channel 26 is configured for movable disposal of a portion of a member, such as, for example, a shaft 28, as described herein. Channel 26 is configured to facilitate translation of shaft 28 relative to wall 22 to move a cutting element 30 between a retracted position and an extended position, as described herein. In some embodiments, channel 26 may have various cross section configurations, such as, for example, circular, cylindrical, oval, oblong, triangular, rectangular, square, polygonal, irregular, uniform, non-uniform, variable, tubular and/or tapered.

Housing 20 includes a surface 32 that defines a cavity, such as, for example, a passageway 34. Passageway 34 is configured for movable disposal of cutting element 30 between a retracted position and an extended position relative to housing 20, as described herein. Surface 32 includes a lateral wall 36 and a lateral wall 38 that define passageway 34. Walls 36, 38 each extend laterally and in a planar configuration from housing 20. In some embodiments, wall 36 and/or wall 38 may extend from housing 20 in alternate configurations, such as, for example, angled, converging, diverging, offset and staggered.

Wall 36 includes a surface 40 that defines a slot 42. Slot 42 includes a linear portion 42a and an arcuate portion 42b. Slot 42 is configured for movable disposal of a pin 74 disposed with cutting element 30, as described herein. Engagement of pin 74 with the surfaces that define portion 42a facilitates translation of cutting element 30 along axis X1 and engagement of pin 74 with the surfaces that define portion 42b facilitates rotation of cutting element 30 relative to axis X1 to pivot a cutting blade of cutting element 30 for removal of tissue, as described herein.

In some embodiments, surface 40 includes a proximal end that defines a proximal stop of slot 42 engageable with pin 74 and/or a distal end that defines a distal stop of slot 42 engageable with pin 74 to resist and/or prevent translation of shaft 28 and/or cutting element 30 in a selected direction and/or beyond a selected limit. In some embodiments, the stops of slot 42 define a selected range of movement of shaft 28 and/or cutting element 30. In some embodiments, the stops of slot 42 can resist and/or prevent translation of shaft 28 in a proximal direction, and translation of cutting element 30 in a distal direction, for example, to resist and/or prevent engagement of cutting element 30 with selected tissue and/or portions of selected tissue.

Wall 38 includes a surface 44 that defines a slot 46. Slot 46 includes a linear portion 46a and an arcuate portion 46b. In some embodiments, slot 46 is disposed contra-lateral to slot 42 relative to axis X1. Slot 46 is configured for movable disposal of a pin 75 disposed with cutting element 30, as described herein. Engagement of pin 75 with the surfaces that define portion 46a facilitates translation of cutting element 30 along axis X1 and engagement of pin 75 with the surfaces that define portion 46b facilitates rotation of cutting element 30 relative to axis X1 to pivot a cutting blade of cutting element 30 for removal of tissue, as described herein.

In some embodiments, surface 44 includes a proximal end that defines a proximal stop of slot 46 engageable with pin 75 and/or a distal end that defines a distal stop of slot 46 engageable with pin 75 to resist and/or prevent translation of shaft 28 and/or cutting element 30 in a selected direction and/or beyond a selected limit. In some embodiments, the stops of slot 46 define a selected range of movement of shaft 28 and/or cutting element 30. In some embodiments, the stops of slot 46 can resist and/or prevent translation of shaft 28 in a proximal direction, and translation of cutting element 30 in a distal direction, for example, to resist and/or prevent engagement of cutting element 30 with selected tissue and/or portions of selected tissue.

Wall 36 includes a surface 50 that defines a slot 52. Slot 52 includes a linear configuration extending along axis X1. Slot 52 is configured for movable disposal of a pin hinge 68 disposed with shaft 28 and cutting element 30, as described herein. In some embodiments, cutting element 30 includes a proximal end that defines an opening for disposal of pin hinge 68 and shaft 28 includes a distal end that defines an opening 65 for disposal of pin hinge 68 such that pin hinge 68 connects shaft 28 and cutting element 30 for relative movement. In some embodiments, the proximal end of cutting element 30 is bifurcated and defines spaced apart openings 84, 86 for disposal of pin hinge 68. In some embodiments, the proximal end of cutting element 30 is bifurcated and defines an intermediate cavity for disposal of the distal end of shaft 28.

Slot 52 is configured to facilitate translation of cutting element 30 along axis X1. Engagement of pin hinge 68 with the surfaces that define slot 52 facilitates translation of cutting element 30 along axis X1. As pins 74, 75 engage the surfaces that define portions 42b, 46b, pins 74, 75 draw and/or rotate cutting element 30 in a transverse direction such that engagement of pin hinge 68 with the surfaces that define slot 52 rotates cutting element 30 about a pivot axis defined by pin hinge 68 relative to axis X1 to pivot a cutting blade of cutting element 30 for removal of tissue, as described herein.

In some embodiments, surface 50 includes a proximal end that defines a proximal stop of slot 52 engageable with pin hinge 68 and/or a distal end that defines a distal stop of slot 52 engageable with pin hinge 68 to resist and/or prevent translation of shaft 28 and/or cutting element 30 in a selected direction and/or beyond a selected limit. In some embodiments, the stops of slot 52 define a selected range of movement of shaft 28 and/or cutting element 30. In some embodiments, the stops of slot 52 can resist and/or prevent translation of shaft 28 in a proximal direction, and translation of cutting element 30 in a distal direction, for example, to resist and/or prevent engagement of cutting element 30 with selected tissue and/or portions of selected tissue.

Wall 38 includes a surface 54 that defines a slot 56. Slot 56 includes a linear configuration extending along axis X1. In some embodiments, slot 56 is disposed contra-lateral to slot 52 relative to axis X1. Slot 56 is configured for movable disposal of pin hinge 68 disposed with shaft 28 and cutting element 30, as described herein. Slot 56 is configured to facilitate translation of cutting element 30 along axis X1. Engagement of pin hinge 68 with the surfaces that define slot 56 facilitates translation of cutting element 30 along axis X1. As pins 74, 75 engage the surfaces that define portions 42b, 46b, pins 74, 75 draw and/or rotate cutting element 30 in a transverse direction such that engagement of pin hinge 68 with the surfaces that define slot 56 rotates cutting element 30 about the pivot axis defined by pin hinge 68 relative to axis X1 to pivot a cutting blade of cutting element 30 for removal of tissue, as described herein.

In some embodiments, surface 54 includes a proximal end that defines a proximal stop of slot 56 engageable with pin hinge 68 and/or a distal end that defines a distal stop of slot 56 engageable with pin hinge 68 to resist and/or prevent translation of shaft 28 and/or cutting element 30 in a selected direction and/or beyond a selected limit. In some embodiments, the stops of slot 56 define a selected range of movement of shaft 28 and/or cutting element 30. In some embodiments, the stops of slot 56 can resist and/or prevent translation of shaft 28 in a proximal direction, and translation of cutting element 30 in a distal direction, for example, to resist and/or prevent engagement of cutting element 30 with selected tissue and/or portions of selected tissue.

In some embodiments, cutting element 30 is rotatable relative to axis X1 to an angle α (FIG. 8) for cutting and/or removal of tissue, as described herein. In some embodiments, angle α is disposable in one or a plurality of angular orientations in an angular range of 0-90 degrees. In some embodiments, angle α is disposable in one or a plurality of angular orientations in an angular range of 0-180 degrees.

Housing 20 includes a fixation element, such as, for example, an awl 60 extending from end 18. Awl 60 extends along axis X1. Awl 60 is configured to anchor surgical instrument 12 with tissue. Awl 60 is configured to pierce and engage tissue to fix surgical instrument 12 with and relative to tissue, as described herein. In some embodiments, awl 60 may extend at alternate orientations relative to housing 20, such as, for example, transverse, perpendicular and/or other angular orientations such as acute or obtuse, co-axial, co-axial with axis X1 and/or may be offset or staggered.

Shaft 28 extends between a proximal end 62 and a distal end 64. Shaft 28 is configured for movable disposal within channel 26. In some embodiments, shaft 28 is disposed co-axial with axis X1. In some embodiments, shaft 28 may extend at alternate orientations relative to axis X1, such as, for example, transverse, perpendicular and/or other angular orientations such as acute or obtuse and/or may be offset or staggered.

End 62 includes a proximal face 66. Proximal face 66 is engageable to axially translate shaft 28 between a retracted position and an extended position, as described herein. In some embodiments, proximal face 66 is engageable with a surgical instrument that strikes face 66 with a dynamic or impact force to cause cutting element 30 to engage selected tissue, as described herein. In some embodiments, proximal face 66 comprises a slap hammer interface engageable with a surgical instrument, such as, for example, an impact surface or hammer that strikes face 66 to cause cutting element 30 to engage selected tissue, as described herein.

End 64 is articulated with cutting element 30 by pin hinge 68. End 64 includes an opening 65 in communication with openings 84, 86, as described herein, configured for movable disposal of pin hinge 68. Pin hinge 68 is configured to facilitate translation of cutting element 30 along slots 52, 56 and rotation of cutting element 30, as described herein.

Cutting element 30 extends between an end 70 and an end 72. In some embodiments, cutting element 30 is bifurcated and includes arms 80, 82 that define a cavity configured for disposal of shaft 28. Arm 80 includes pin 74 and arm 82 includes pin 75. Pin 74 is engageable with slot 42 and pin 75 is engageable with slot 46 to facilitate translation and rotation of cutting element 30 relative to axis X1 along slots 42, 46. Arm 80 includes opening 84 configured for disposal of pin hinge 68. Arm 82 includes opening 86 configured for disposal of pin hinge 68. Pin hinge 68 is disposed with cutting element 30 and shaft 28 to facilitate relative translation and rotation thereof.

End 72 includes a wall 76 that extends to a cutting surface, such as, for example, a blade 78. As cutting element 30 is rotated, as described herein, wall 76 engages cut tissue and rotates relative to the pivot axis, shaft 28, housing 20 and/or axis X1 to transversely move cut tissue and/or displace cut tissue laterally from the site of the cut tissue. In some embodiments, wall 76 has a tapered surface configuration. In some embodiments, wall 76 has a planar surface configuration. In some embodiments, wall 76 has an arcuate surface configuration. Blade 78 is configured to disrupt, scrape, cut and/or remove tissue from a surgical site and/or one or more surfaces of housing 20.

Upon engagement of proximal face 66 with a dynamic or impact force, shaft 28 translates axially between a retracted position and an extended position, as described herein. Shaft 28 translates cutting element 30 via connection with pin hinge 68. Pins 74, 75 translate along portions 42a, 46a and pin hinge 68 translates along slots 52, 56 such that wall 76 and blade 78 translate, in a direction shown by arrow A in FIG. 6. Wall 76 and blade 78 extend beyond end 18, as shown in FIG. 7, to engage selected tissue, as described herein. Blade 78 engages selected tissue to disrupt, scrape, cut and/or remove the selected tissue.

Figure 8:
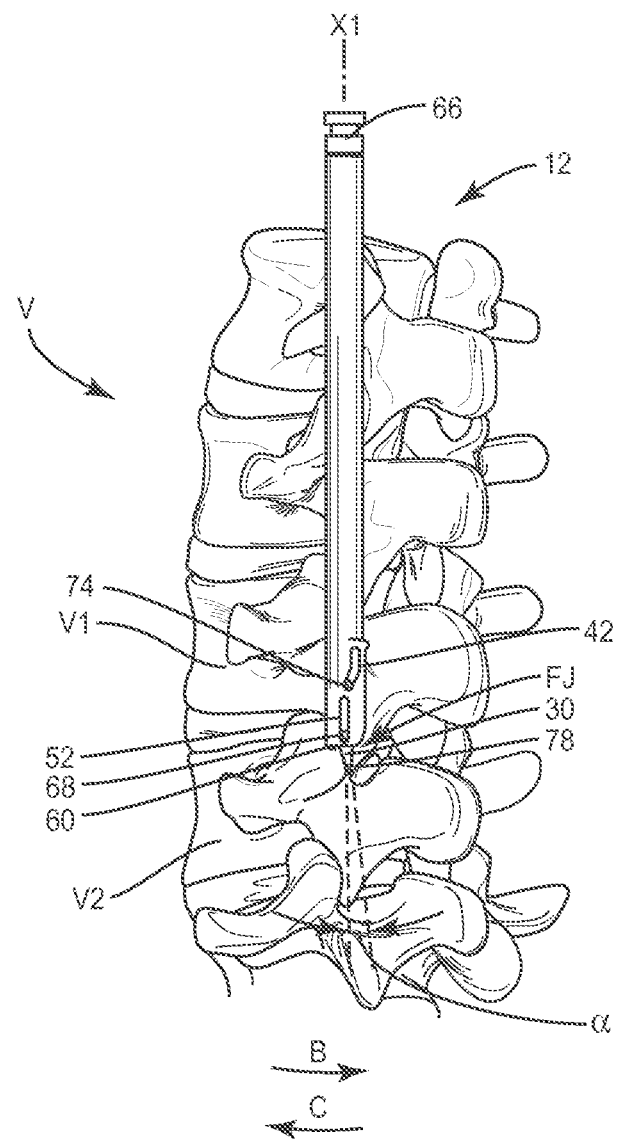
FIG. 8 is a perspective view of components of one embodiment of a surgical system in accordance with the principles of the present disclosure disposed with vertebrae.
Figure 9:
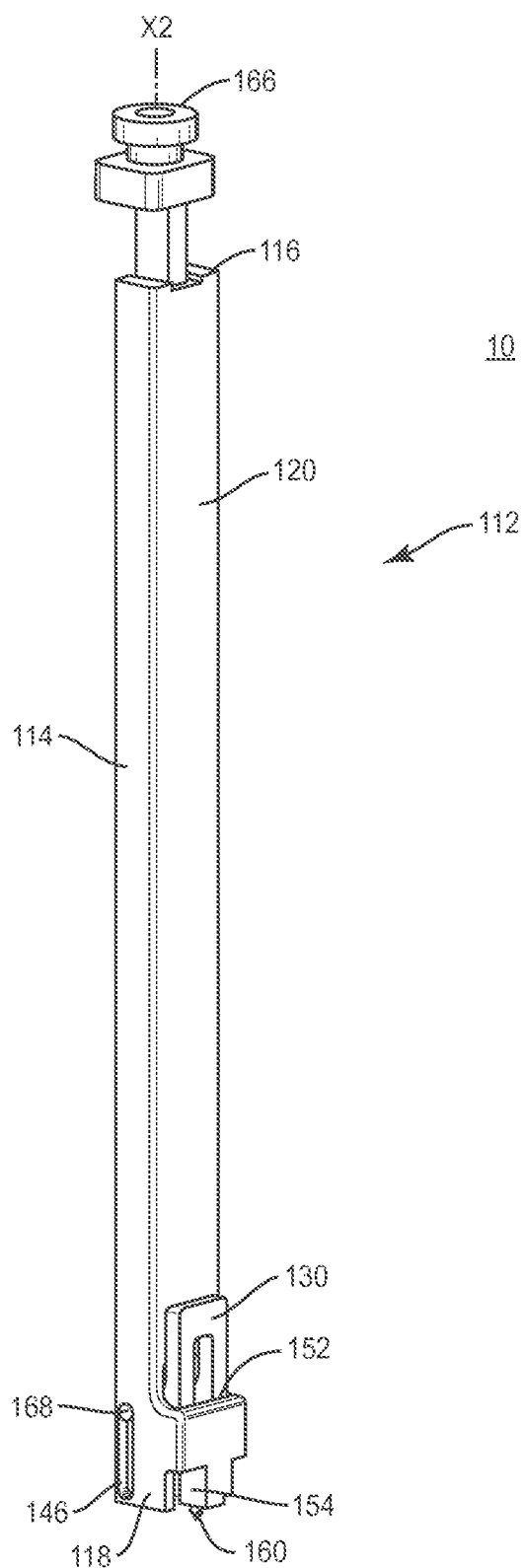
FIG. 9 is a perspective view of components of one embodiment of a surgical system in accordance with the principles of the present disclosure.
Figure 10:
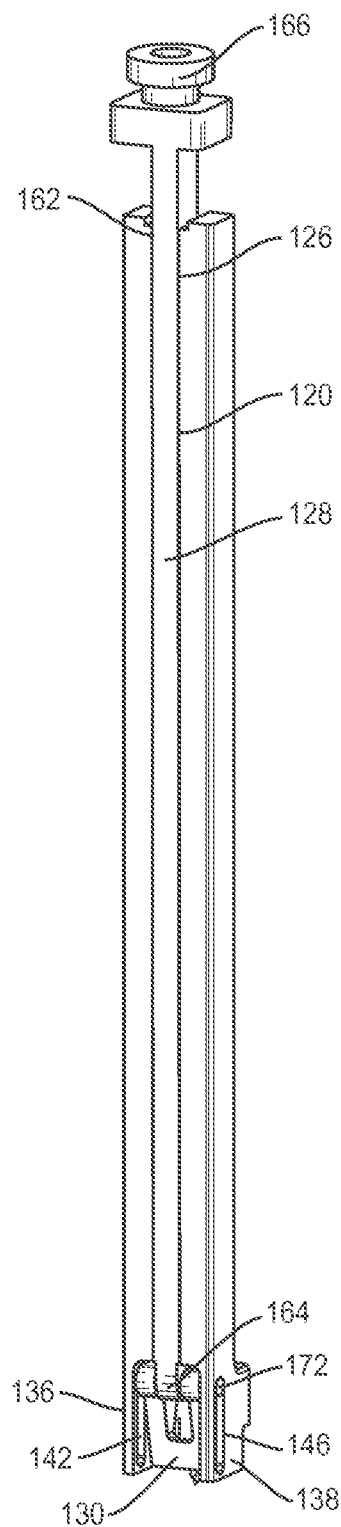
FIG. 10 is a perspective view of the components shown in FIG. 9.

Pins 74, 75 engage the surfaces that define portions 42b, 46b to rotate cutting element 30 and pin hinge 68 engages the surfaces that define slots 52, 56 such that wall 76 rotates about the pivot axis defined by pin hinge 68 relative to axis X1, in a direction shown by arrow B in FIG. 8, to pivot wall 76 and transversely move cut tissue and/or displace cut tissue laterally.

Figure 6:
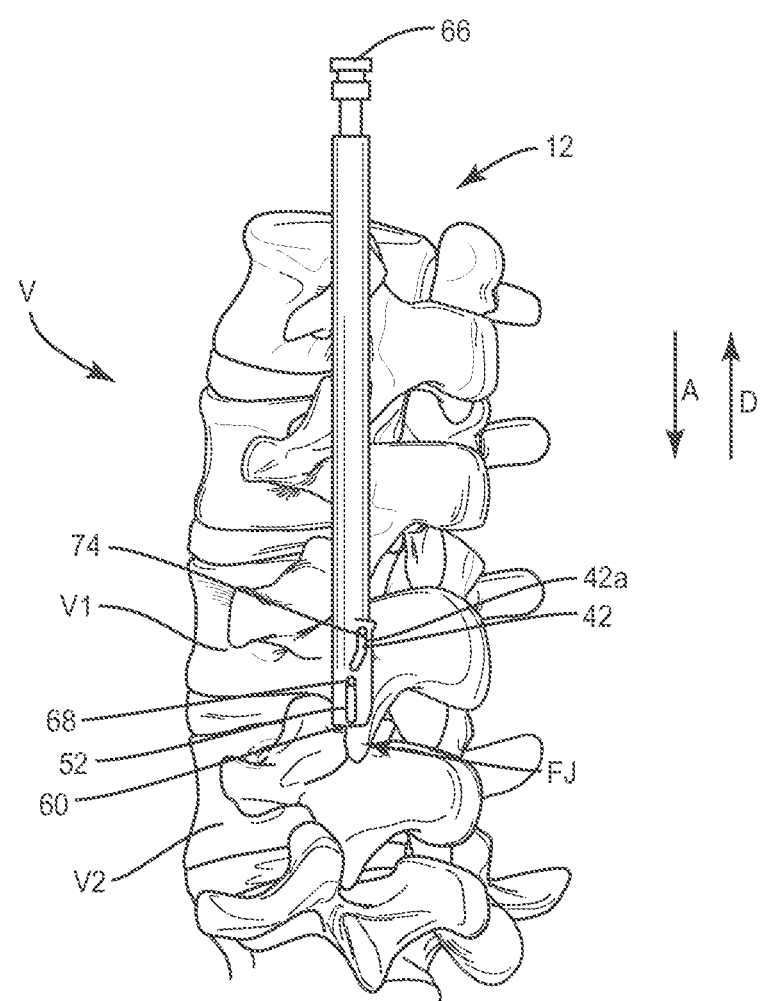
FIG. 6 is a perspective view of components of one embodiment of a surgical system in accordance with the principles of the present disclosure disposed with vertebrae.
Figure 7:
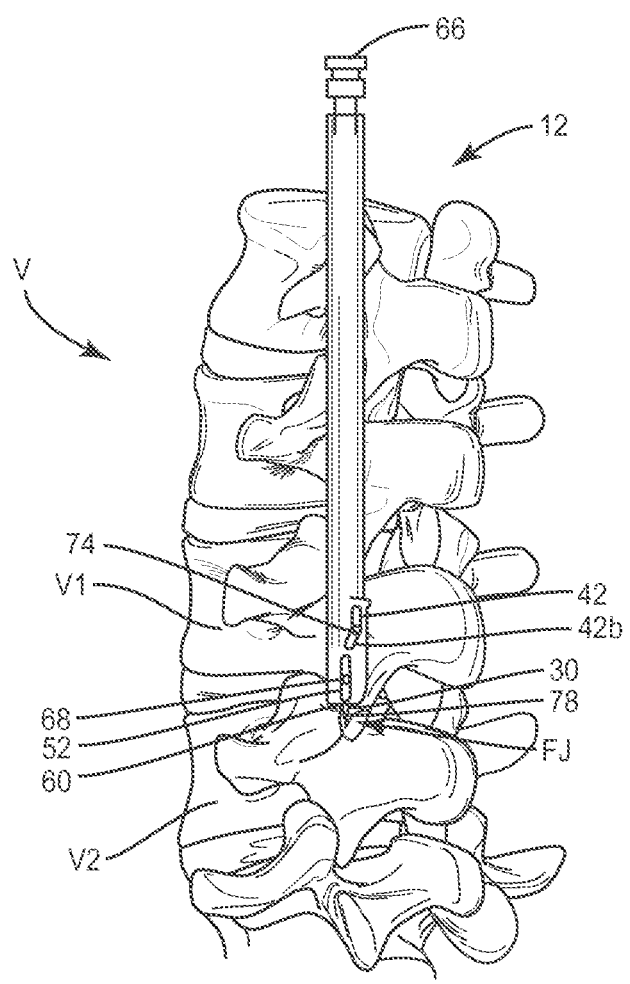
FIG. 7 is a perspective view of components of one embodiment of a surgical system in accordance with the principles of the present disclosure disposed with vertebrae.

In assembly, operation and use, as shown in FIGS. 6-8, surgical system 10, similar to the systems and methods described herein, is employed to treat an affected section of vertebrae V. A medical practitioner obtains access to a surgical site including vertebrae V in any appropriate manner, such as through incision and retraction of tissues. The components of surgical system 10 including surgical instrument 12 are employed to augment a surgical treatment. Surgical instrument 12 can be delivered to a surgical site as a pre-assembled device or can be assembled in situ. Surgical system 10 may be completely or partially revised, removed or replaced.

An incision is made in the body of a patient and a cutting instrument (not shown) creates a surgical pathway for preparation and/or removal of tissue surfaces in connection with surgical treatment, and/or implantation of components of surgical system 10 with a portion of vertebrae V including vertebrae V1, V2 and facet joint FJ. Surgical instruments can be employed to prepare tissue surfaces of vertebrae V, as well as for aspiration and irrigation of a surgical region.

Surgical instrument 12 is delivered to the surgical site including vertebrae V and adjacent facet joint FJ. Awl 60 is engaged with tissue adjacent facet joint FJ to anchor surgical instrument 12 in fixed relation with vertebral tissue adjacent facet joint FJ. Housing 20 is manipulated including rotation, translation and/or angulation of housing 20 for engagement with vertebral tissue adjacent facet joint FJ.

Shaft 28 is disposed in a retracted position, as shown in FIG. 6, such that pins 74, 75 engage proximal stops of slots 42, 46 and pin hinge 68 engages proximal stops of slots 52, 56. Cutting element 30 is disposed within passageway 34. In some embodiments, wall 76 is disposed in parallel alignment with axis X1 in the retracted position.

A surgical hammer (not shown) engages proximal face 66 with a dynamic or impact force and shaft 28 translates axially from the retracted position to an extended position, as shown in FIG. 7. Shaft 28 translates cutting element 30 axially such that pins 74, 75 translate along portions 42a, 46a and pin hinge 68 translates along slots 52, 56. Wall 76 and blade 78 translate, in a direction shown by arrow A in FIG. 6. Wall 76 and blade 78 extend beyond end 18, as shown in FIG. 7, to engage tissue of facet joint FJ for removal of selected facet tissue. Blade 78 engages selected facet tissue to disrupt, scrape, cut and/or remove the selected facet tissue.

Pins 74, 75 engage the surfaces that define portions 42b, 46b to rotate cutting element 30 and pin hinge 68 engages the surfaces that define slots 52, 56 such that wall 76 rotates about the pivot axis defined by pin hinge 68 relative to axis X1, in a direction shown by arrow B in FIG. 8, to pivot wall 76 and transversely move cut tissue of facet joint FJ and displace the cut tissue of facet joint FJ laterally from the surgical site. Cutting element 30 displaces the cut tissue laterally to a movable limit as defined by engagement of pins 74, 75 with distal stops of slots 42, 46 and engagement of pin hinge 68 with distal stops of slots 52, 56.

In some embodiments, the cut tissue is suctioned or aspirated from the surgical site. Shaft 28 is translated axially, in a direction shown by arrow D in FIG. 6, to the retracted position. Cutting element 30 is rotated, in a direction shown by arrow C in FIG. 8, about the pivot axis of pin hinge 68 relative to axis X1 and translated, in a direction shown by arrow D in FIG. 6, via engagement of pins 74, 75 with slots 42, 46 and engagement of pin hinge 68 with slots 52, 56 to retract wall 76 and blade 78 into passageway 34. In some embodiments, surgical system 10 includes one or a plurality of implants, such as, for example, interbody devices, rods, plates, connectors and/or bone fasteners that are delivered to the surgical site for use with a single vertebral level or a plurality of vertebral levels.

In some embodiments, housing 20 includes a biasing member such that shaft 28 is biased for translation to the retracted position and/or the extended position. In some embodiments, the biasing member may have a semi-rigid, rigid or elastic configuration, and/or have elastic properties, such as the elastic properties corresponding to the material examples described above, such that the biasing member provides a selective amount of expansion, contraction, collapse and/or extension. In some embodiments, the biasing member may include a plurality of separately attachable or connectable portions or sections, such as bands or loops, or may be monolithically formed as a single continuous element. In some embodiments, the biasing member includes an axial element, such as, for example, a flexible shaft. In some embodiments, the biasing member has a solid disc or sphere shape. In some embodiments, the biasing member has a tubular wall. In some embodiments, the biasing member may include a coil spring, an elastomeric member, clip, leaf spring, gravity induced configuration, pneumatic configuration, hydraulic configuration and/or manual lever.

In some embodiments, surgical system 10 can include one or more surgical instruments for use with surgical instrument 12, such as, for example, drivers, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed, coated or layered within, on or about the components and/or surfaces of surgical system 10. In some embodiments, the agent may include bone growth promoting material, such as, for example, bone graft to enhance fixation of the components and/or surfaces of surgical system 10 with vertebrae V. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of surgical system 10 are removed and the incision is closed. The components of surgical system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical system 10.

In one embodiment, as shown in FIGS. 9-14, surgical system 10, similar to the systems and methods described herein, includes a surgical instrument 112, similar to surgical instrument 12 described with regard to FIGS. 1-8.

Surgical instrument 112 includes a member, such as, for example, a body 114, similar to body 14 described herein, which extends between an end 116 and an end 118. Body defines an axis X2 and includes a housing 120. Housing 120 includes a wall 122 that includes an inner surface 124. Surface 124 defines a channel 126 extending along axis X2. Channel 126 extends between ends 116, 118. Channel 126 is configured for movable disposal of a shaft 128, similar to shaft 28 described herein. Channel 126 is configured to facilitate translation of shaft 128 relative to wall 122 to move a cutting element 130, similar to cutting element 30 described herein, between a retracted position and an extended position, similar to that described herein.

Shaft 128 defines a plurality of spaced apart slots 152. Slots 152 each includes a linear configuration extending along axis X2. Each of slots 152 is configured for movable disposal of a pin 153. Pins 153 are disposed with shaft 128 and housing 120 to facilitate axial translation of shaft 128 relative to housing 120 along axis X2. In some embodiments, slots 152 each include a proximal end that defines a proximal stop of slot 152 engageable with pin 153 and/or a distal end that defines a distal stop of slot 152 engageable with pin 153 to resist and/or prevent translation of shaft 128 and/or cutting element 130 in a selected direction and/or beyond a selected limit. In some embodiments, the stops of slot 152 define a selected range of movement of shaft 128 and/or cutting element 130. In some embodiments, the stops of slot 152 can resist and/or prevent translation of shaft 128 in a proximal direction, and translation of cutting element 130 in a distal direction, for example, to resist and/or prevent engagement of cutting element 130 with selected tissue and/or portions of selected tissue.

Housing 120 includes a surface 132 that defines a passageway 134, which is configured for movable disposal of cutting element 130. Surface 132 includes a lateral wall 136 and a lateral wall 138 that define passageway 134. Wall 136 includes a surface 140 that defines a slot 142. Slot 142 includes a linear configuration extending along axis X2. Slot 142 is configured for movable disposal of a pin hinge 168 disposed with shaft 128 and cutting element 130, as described herein. In some embodiments, cutting element 130 includes an opening for disposal of pin hinge 168 and shaft 128 includes a distal end that defines an opening 165 for disposal of pin hinge 168 such that pin hinge 168 connects shaft 128 and cutting element 130 for relative movement.

Slot 142 is configured to facilitate translation of cutting element 130 along axis X2. Engagement of pin hinge 168 with the surfaces that define slot 142 facilitates translation of cutting element 130 along axis X2. As pin hinge 168 engages the surfaces that define slot 142, cutting element 130 engages housing 120 and rotates about a pivot axis defined by pin hinge 168 relative to axis X2 to pivot a cutting blade of cutting element 130 for removal of tissue, as described herein.

In some embodiments, surface 140 includes a proximal end that defines a proximal stop of slot 142 engageable with pin hinge 168 and/or a distal end that defines a distal stop of slot 142 engageable with pin hinge 168 to resist and/or prevent translation of shaft 128 and/or cutting element 130 in a selected direction and/or beyond a selected limit. In some embodiments, the stops of slot 142 define a selected range of movement of shaft 128 and/or cutting element 130. In some embodiments, the stops of slot 142 can resist and/or prevent translation of shaft 128 in a proximal direction, and translation of cutting element 130 in a distal direction, for example, to resist and/or prevent engagement of cutting element 130 with selected tissue and/or portions of selected tissue.

Wall 138 includes a surface 144 that defines a slot 146. Slot 146 includes a linear configuration extending along axis X2. In some embodiments, slot 146 is disposed contralateral to slot 142 relative to axis X2. Slot 146 is configured for movable disposal of pin hinge 168 disposed with shaft 128 and cutting element 130, as described herein. Slot 146 is configured to facilitate translation of cutting element 130 along axis X2. Engagement of pin hinge 168 with the surfaces that define slot 146 facilitates translation of cutting element 130 along axis X2. As pin hinge 168 engages the surfaces that define slot 146, cutting element 130 engages housing 120 and rotates about the pivot axis defined by pin hinge 168 relative to axis X2 to pivot a cutting blade of cutting element 130 for removal of tissue, as described herein.

In some embodiments, surface 144 includes a proximal end that defines a proximal stop of slot 146 engageable with pin hinge 168 and/or a distal end that defines a distal stop of slot 146 engageable with pin hinge 168 to resist and/or prevent translation of shaft 128 and/or cutting element 130 in a selected direction and/or beyond a selected limit. In some embodiments, the stops of slot 146 define a selected range of movement of shaft 128 and/or cutting element 130. In some embodiments, the stops of slot 146 can resist and/or prevent translation of shaft 128 in a proximal direction, and translation of cutting element 130 in a distal direction, for example, to resist and/or prevent engagement of cutting element 130 with selected tissue and/or portions of selected tissue.

Housing 120 includes a surface 150 that defines a projection, such as, for example, a track 154. Track 154 is configured for engagement with a portion of cutting element 130, such as, for example, surfaces that define a slot 190. Slot 190 includes a linear configuration extending along axis X2. Engagement of track 154 with the surfaces that define slot 190 facilitates translation of cutting element 130 along axis X2. Track 154 includes a head 155. As the surfaces that define slot 190 engage head 155, track 154 drives cutting element 130 to rotate, in a direction shown by arrows G in FIG. 14, within passageway 134.

Housing 120 defines a cavity 162 configured for disposal of a portion 164 of cutting element 130, as described herein. As the surfaces that define slot 190 engage head 155, cutting element 130 pivots about the pivot axis defined by pin hinge 168 relative to axis X2 such that portion 164 rotates into cavity 162 to pivot a cutting blade of cutting element 130 for removal of tissue, similar to that described herein.

In some embodiments, cutting element 130 is rotatable relative to axis X2 to an angle β (FIG. 14) for cutting and/or removal of tissue, as described herein. In some embodiments, angle β is disposable in one or a plurality of angular orientations in an angular range of 0-90 degrees. In some embodiments, angle β is disposable in one or a plurality of angular orientations in an angular range of 0-180 degrees.

Housing 120 includes a fixation element, such as, for example, an awl 160, similar to awl 60 described herein, extending from end 118. Shaft 128 extends between a proximal end 162 and a distal end 163. Shaft 128 is configured for movable disposal within channel 126. End 162 includes a proximal face 166, similar to proximal face 66 described herein.

End 163 is articulated with cutting element 130 by pin hinge 168. End 163 includes an opening 165 in communication with openings 184, 186, as described herein, configured for movable disposal of pin hinge 168. Pin hinge 168 is configured to facilitate translation of cutting element 130 along slots 142, 146 and rotation of cutting element 130, as described herein.

Cutting element 130 extends between an end 170 and an end 172. Pin hinge 168 is engageable with slot 142 and slot 146 to facilitate translation and rotation of cutting element 130 relative to axis X2 along slots 142, 146. End 172 includes a wall 176 that extends to a blade 178. As cutting element 130 is rotated, as described herein, wall 176 engages cut tissue and rotates relative to the pivot axis, shaft 128, housing 120 and/or axis X2 to transversely move cut tissue and/or displace cut tissue laterally from the site of the cut tissue.

Figure 13:
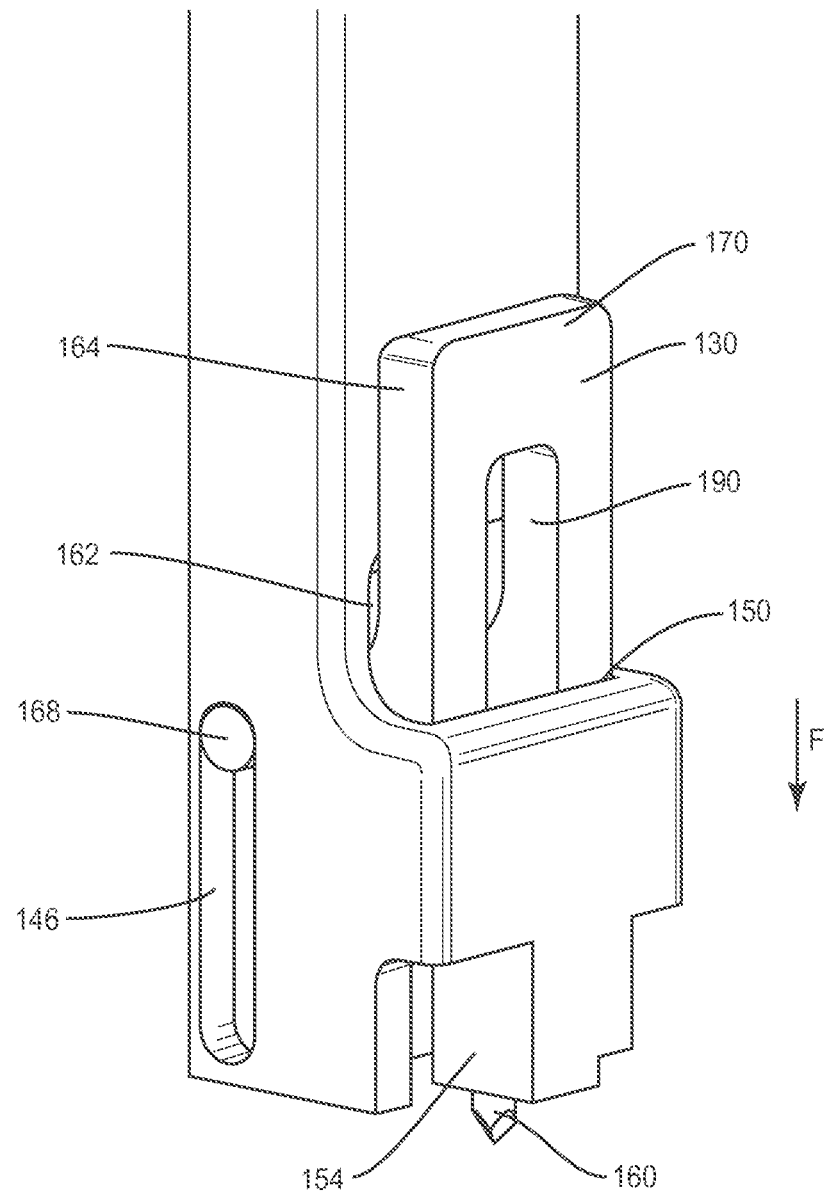
FIG. 13 is an enlarged, break away view of the components shown in FIG. 9.

Upon engagement of proximal face 166 with a dynamic or impact force, shaft 128 translates axially between a retracted position and an extended position, as described herein. Shaft 128 translates cutting element 130 via connection with pin hinge 168 with slots 142, 146 and connection of track 154 with slot 190. Pin hinge 168 translates along slots 142, 146 and slot 190 translates along track 154, in a direction shown by arrow F in FIG. 13. Wall 176 and blade 178 extend beyond end 118, as shown in FIG. 13, to engage selected tissue, as described herein. Blade 178 engages selected tissue to disrupt, scrape, cut and/or remove the selected tissue.

Figure 14:
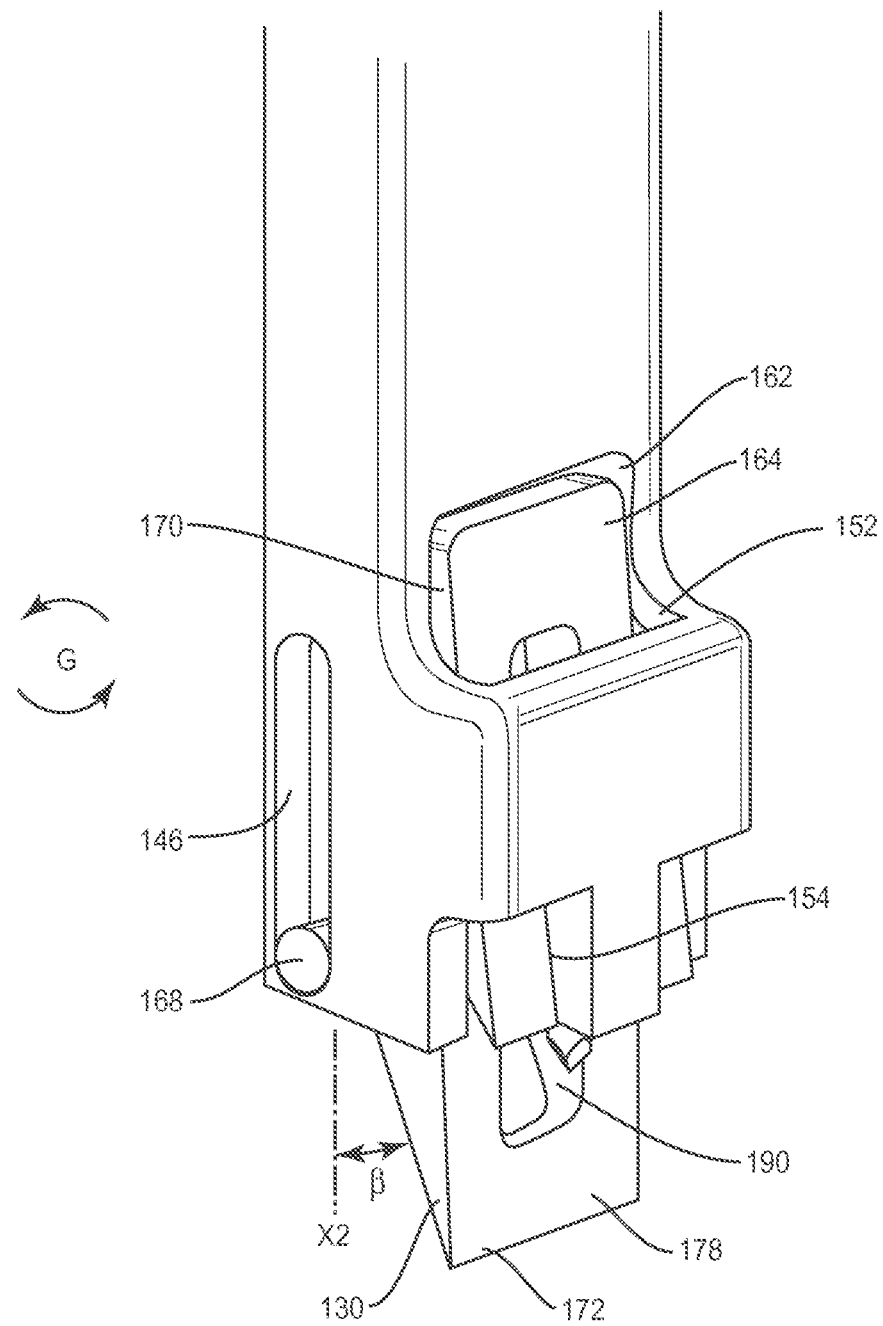
FIG. 14 is an enlarged, break away view of the components shown in FIG. 9.

As cutting element 130 pivots into cavity 162, cutting element 130 rotates, in a direction shown by arrows G in FIG. 14. Pin hinge 168 engages the surfaces that define slots 142, 146 to rotate cutting element 130 such that wall 176 rotates about the pivot axis defined by pin hinge 168 relative to axis X2, in the direction shown by arrows G, to pivot wall 176 and transversely move cut tissue and/or displace cut tissue laterally.

Shaft 128 defines a slot 180, which includes a linear configuration extending along axis X2. Slot 180 is configured for movable disposal of a pin 182. Pin 182 is disposed with shaft 128 and housing 120 to facilitate axial translation of shaft 128 relative to housing 120 along axis X2. In some embodiments, slot 180 includes a proximal end that defines a proximal stop of slot 180 engageable with pin 182 and/or a distal end that defines a distal stop of slot 180 engageable with pin 182 to resist and/or prevent translation of shaft 128 and/or cutting element 130 in a selected direction and/or beyond a selected limit. In some embodiments, the stops of slot 180 define a selected range of movement of shaft 128 and/or cutting element 130. In some embodiments, the stops of slot 180 can resist and/or prevent translation of shaft 128 in a proximal direction, and translation of cutting element 130 in a distal direction, for example, to resist and/or prevent engagement of cutting element 130 with selected tissue and/or portions of selected tissue.

Figure 11:
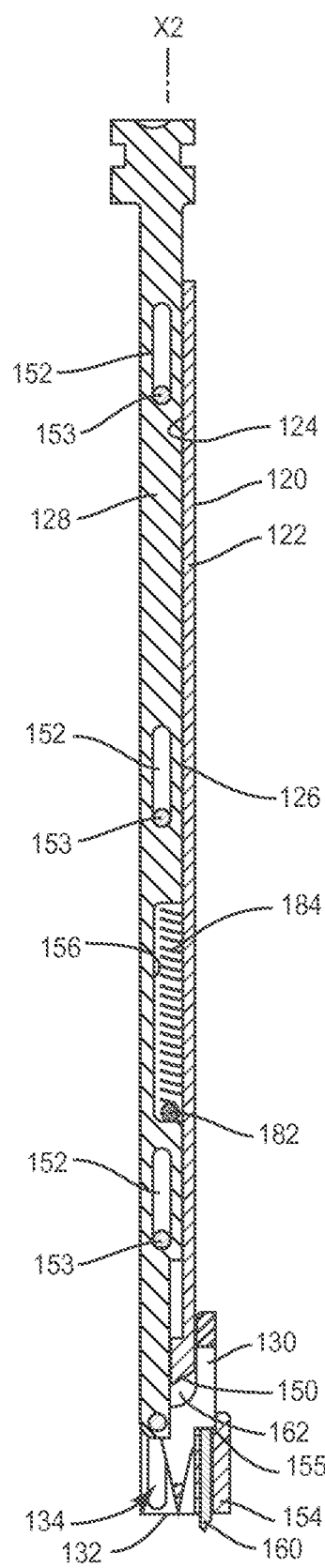
FIG. 11 is a cross section view of the components shown in FIG. 9.
Figure 12:
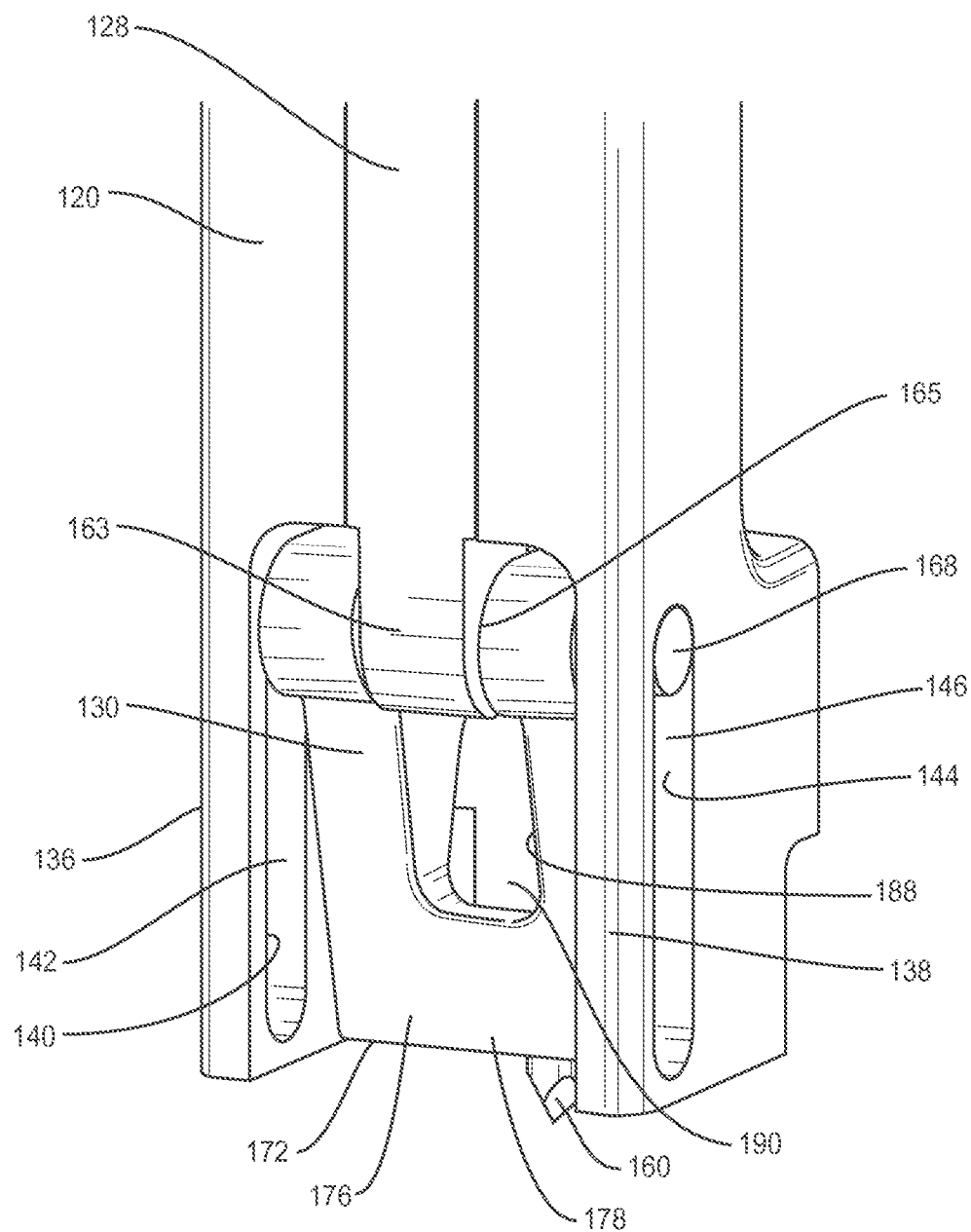
FIG. 12 is an enlarged, break away view of the components shown in FIG. 9.

Slot 180 includes a biasing member, such as, for example, a coil spring 184 to bias shaft 128 for translation to the retracted position, as shown in FIG. 11. In some embodiments, the biasing member can bias shaft 128 to an extended position. In some embodiments, the biasing member may have a semi-rigid, rigid or elastic configuration, and/or have elastic properties, such as the elastic properties corresponding to the material examples described above, such that the biasing member provides a selective amount of expansion, contraction, collapse and/or extension. In some embodiments, the biasing member may include a plurality of separately attachable or connectable portions or sections, such as bands or loops, or may be monolithically formed as a single continuous element. In some embodiments, the biasing member includes an axial element, such as, for example, a flexible shaft. In some embodiments, the biasing member has a solid disc or sphere shape. In some embodiments, the biasing member has a tubular wall. In some embodiments, the biasing member may include an elastomeric member, clip, leaf spring, gravity induced configuration, pneumatic configuration, hydraulic configuration and/or manual lever.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
 a first member extending along a longitudinal axis between opposite first and second ends, the first member defining a passageway extending along the longitudinal axis, the second end including a cavity in communication with the passageway and a slot in communication with the cavity;
 a second member disposed in the passageway; and
 a cutting element connected with the second member by a pin, the pin extending through the slot and the cutting element,
 wherein the second member is configured to translate along the longitudinal axis to translate the pin along the slot and rotate the cutting element relative to the second member.

2. The surgical instrument recited in claim 1, wherein the cutting element is rotatable relative to the second member between a retracted position and an extended position, the cutting element being disposed entirely within the cavity when the cutting element is in the retracted position.

3. The surgical instrument recited in claim 1, wherein the slot defines a range of translation of the second member relative to the first member.

4. The surgical instrument recited in claim 1, wherein the slot includes a linear portion and an arcuate portion.

5. The surgical instrument recited in claim 4, wherein the linear portion extends parallel to the longitudinal axis.

6. The surgical instrument recited in claim 1, wherein the slot is a first slot, the surgical instrument comprising a pin and a second slot, the pin extending through the second slot and the cutting element, the second slot being spaced apart from the first slot.

7. The surgical instrument recited in claim 6, wherein the second slot has a linear configuration.

8. The surgical instrument recited in claim 6, wherein the second slot extends parallel to the longitudinal axis.

9. The surgical instrument recited in claim 6, wherein a proximal end of the cutting element is bifurcated and defines space apart openings for disposal of the pin.

10. The surgical instrument recited in claim 6, wherein engagement of the pin with surfaces that define the second slot rotates the cutting element about a pivot axis defined by the pin relative to the longitudinal axis.

11. The surgical instrument recited in claim 1, wherein a portion of the cavity is defined by an opening that is coaxial with the longitudinal axis, the opening extending through an exterior end surface of the second end, the exterior end surface extending perpendicular to the longitudinal axis.

12. The surgical instrument recited in claim 1, wherein the first end comprises an end surface and the second end comprises a housing, the housing including the cavity and the slot, the first member having a uniform diameter from the end surface to the housing.

13. The surgical instrument recited in claim 1, wherein the second member comprises a first end and an opposite second end that is connected with the cutting element, the first end of the second member having a diameter greater than a diameter of the passageway.

14. The surgical instrument recited in claim 1, wherein the first member is monolithic.

15. The surgical instrument recited in claim 1, wherein the first member is monolithic, an inner surface of the first member defining the passageway, an outer surface of the second member directly engaging the inner surface when the second member is disposed in the passageway.

16. The surgical instrument recited in claim 1, wherein the first member comprises an outer surface and an opposite inner surface defining the passageway, the first end being free of any grooves or recesses extending into the outer surface.

17. The surgical instrument recited in claim 1, wherein the second member is monolithic.

18. The surgical instrument recited in claim 1, wherein an exterior end surface of the second end extends perpendicular to the longitudinal axis, the first member comprising a spike extending outwardly from the exterior end surface.

19. A surgical instrument comprising:
 a first member extending along a longitudinal axis between opposite first and second ends, the first member defining a passageway extending along the longitudinal axis, the second end including a housing, the housing defining a cavity in communication with the passageway and a slot in communication with the cavity, the first member comprising an end surface, the first member having a uniform diameter from the end surface to the housing;

a second member comprises a first end and an opposite second end that is disposed in the passageway, the first end of the second member having a diameter greater than a diameter of the passageway; and a cutting element connected with the second end of the second member by a pin, the pin extending through the slot and the cutting element, wherein the second member is configured to translate along the longitudinal axis to translate the pin along the slot and rotate the cutting element relative to the second member.

20. A surgical instrument comprising:

a first member extending along a longitudinal axis between opposite first and second ends, the first member defining a passageway extending along the longitudinal axis, the second end including a housing, the housing defining a cavity in communication with the passageway and spaced apart first and second slots that are each in communication with the cavity;

a second member disposed in the passageway; and a cutting element connected with the second member by a pin and a hinge pin, the pin extending through the first slot and the cutting element, the hinge pin extending through the second slot and the cutting element, wherein the first slot includes a linear portion and an arcuate portion, the linear portion extending parallel to the longitudinal axis, wherein the second slot extends parallel to the longitudinal axis, and wherein the second member is configured to translate along the longitudinal axis to translate the pin along the first slot such that the cutting element rotates in a transverse direction and engagement of the pin with surfaces that define the second slot rotates the cutting element about a pivot axis defined by the hinge pin.

* * * * *

UNITED STATES PATENT AND TRADEMARK OFFICE
CERTIFICATE OF CORRECTION

| | |
|---|---|
| PATENT NO. | : 11,369,389 B2 |
| APPLICATION NO. | : 16/725250 |
| DATED | : June 28, 2022 |
| INVENTOR(S) | : Stanley T. Palmatier et al. |

It is certified that error appears in the above-identified patent and that said Letters Patent is hereby corrected as shown below:

In the Claims

Column 14, Line 23, "space" should read --spaced--.

Signed and Sealed this
Twenty-third Day of August, 2022

Katherine Kelly Vidal
*Director of the United States Patent and Trademark Office*